United States Patent
Walsh et al.

(10) Patent No.: US 8,773,662 B2
(45) Date of Patent: Jul. 8, 2014

(54) METHODS AND APPARATUS FOR VACUUM ULTRAVIOLET (VUV) OR SHORTER WAVELENGTH CIRCULAR DICHROISM SPECTROSCOPY

(75) Inventors: Phillip Walsh, Austin, TX (US);
Anthony T. Hayes, Leander, TX (US);
Dale A. Harrison, Austin, TX (US)

(73) Assignee: VUV Analytics, Inc., Austin, TX (US)

( * ) Notice: Subject to any disclaimer, the term of this patent is extended or adjusted under 35 U.S.C. 154(b) by 330 days.

(21) Appl. No.: 13/184,619

(22) Filed: Jul. 18, 2011

(65) Prior Publication Data

US 2012/0268740 A1 Oct. 25, 2012

Related U.S. Application Data

(60) Provisional application No. 61/400,153, filed on Jul. 22, 2010.

(51) Int. Cl.
*G01J 4/00* (2006.01)
*G01N 21/19* (2006.01)

(52) U.S. Cl.
CPC ..................... *G01N 21/19* (2013.01)
USPC .......................................................... 356/364

(58) Field of Classification Search
CPC .......................... G02B 17/0852; G02B 27/126
USPC ................... 356/326, 327, 364, 368
See application file for complete search history.

(56) References Cited

U.S. PATENT DOCUMENTS

| | | | |
|---|---|---|---|
| 3,450,478 A | 6/1969 | Sebestyen | |
| 3,737,235 A * | 6/1973 | Hawes | 356/453 |
| 5,076,696 A * | 12/1991 | Cohn et al. | 356/369 |
| 5,298,973 A * | 3/1994 | Fukazawa et al. | 356/368 |
| 5,788,632 A * | 8/1998 | Pezzaniti et al. | 600/316 |
| 6,118,536 A * | 9/2000 | Sakamoto et al. | 356/364 |
| 6,180,604 B1 * | 1/2001 | Fraser et al. | 514/2.4 |
| 6,480,277 B1 * | 11/2002 | Nafie | 356/364 |
| 7,002,692 B2 * | 2/2006 | Akao et al. | 356/491 |
| 7,067,818 B2 * | 6/2006 | Harrison | 250/372 |
| 7,292,389 B2 * | 11/2007 | Kaminsky et al. | 359/371 |
| 7,391,030 B2 | 6/2008 | Harrison | |
| 7,485,869 B2 | 2/2009 | Harrison et al. | |
| 7,574,601 B2 | 8/2009 | Jahromi et al. | |
| 7,684,037 B2 * | 3/2010 | Harrison et al. | 356/328 |
| 7,924,436 B2 * | 4/2011 | Mengel et al. | 356/515 |
| 2004/0213443 A1 | 10/2004 | Haussecker et al. | |
| 2009/0198454 A1 * | 8/2009 | Inoue et al. | 702/30 |
| 2010/0245822 A1 | 9/2010 | Garab et al. | |
| 2012/0170021 A1 * | 7/2012 | Walsh | 356/51 |

OTHER PUBLICATIONS

Yamada et al., "Vacuum ultraviolet circular dichroism spectroscopy using an ac-modulated polarizing undulator", Rev. Sci. Instrum. 76, 093103, 2005, pp. 1-7.*

(Continued)

*Primary Examiner* — Gregory J Toatley
*Assistant Examiner* — Shawn Decenzo
(74) *Attorney, Agent, or Firm* — Egan, Peterman, Enders LLP.

(57) ABSTRACT

A highly efficient vacuum ultraviolet circular dichroism spectrometer is provided; the spectrometer suitable for laboratory use or for integration into a beam line at a synchrotron radiation facility. In one embodiment, a spectroscopic circular dichroism instrument is provided; the instrument configured so as to enable circular dichroism data to be simultaneously obtained for multiple wavelengths of light. The instrument may be further configured to operate in at least a portion of the vacuum ultraviolet wavelength region.

17 Claims, 7 Drawing Sheets

(56) References Cited

OTHER PUBLICATIONS

Johnson, "Analyzing Protein Circular Dichroism Spectra for Accurate", Proteins Structure, Function and Genetics, 1999, 6 pgs.
Nijs et al., "Calibration Method for Rotating Analyzer Ellipsometers", J. Opt. Soc. Am.A., vol. 5, No. 9, Sep. 1988, 6 pgs.
Provencher et al., "Estimation of Globular Protein Secondary Structure From Circular Dichroism", American Chemical Society, 1981, 5 pgs.
Sreerama et al., "Estimation of Protein Secondary Structure From Circular Dichroism Spectra: Comparison of Contin, Selcon and CDSSTR Methods With an Expanded Reference Set", Analytical Biochemistry, 2000, 9 pgs.
Sreerama et al., "Computaton and Analysis of Protein Circular Dichroism Spectra", Numerical Computer Methods, 2004, 34 pgs.
Wien et al., "Calcium Fluoride Micro Cells for Synchrotron Radiation Circular Dichroism Spectroscopy", Applied Spectroscopy, 2005, 5 pgs.
Schellman et al., "Optical Spectroscopy of Oriented Molecules", American Chemical Society, 1987, 41 pgs.
Che et al., "Optical Analysis of an Ellipsometric Technique for Time-Resolved Magnetic Circular Dichroism Spectroscopy", American Chemical Society, 1994, 11 pgs.
Collins, "Automatic Rotating Element Ellipsometers: Calibration, Operation, and Real-time Applications", Rev. Sci. Instrum, vol. 61, 8, 1989, 34 pgs.
Sreerama et al., "A Self-Consistent Method for the Analysis of Protein Secondary Structure From Circular Dichroism", Analytical Biochemistry, 1993, 13 pgs.
Hennessey et al., "Experimental Errors and Their Effect on Analyzing Circular Dichroism Spectra of Proteins", Analytical Biochemistry, 1982, 12 pgs.
Johnson, "A Circular Dichroism Spectrometer for the Vacuum Ultraviolet", vol. 42, No. 9, 1971, 4 pgs.
Lewis et al., "New Technique for Measuring Circular Dichroism Changes on a Nansecond Time Scale. Application to Carbonmonoxy Myoglobin and Carbonmonoxy Hemoglobin", J. Phys. Chem., 1985, 6 pgs.
Miles et al., "Calibration and Standardisation of Synchrotron Radiation Circular Dichroism and Conventional Circular Dichroism Spectrophotometers", Spectroscopy, 2993, 10 pgs.
Lee et al., "Alignment and Calibration of the MgF2 Biplate Compensator for Applications in Rotating-Compensator Multichannel Ellipsometry", J. Opt. Soc. Am.A, vol. 18, No. 8, 2001, 6 pgs.
Walsh et al., Search Report, PCT/US12/46613, Sep. 2012, 2 pgs.
Walsh, PCT International Written Opinion, PCT/US2012/046613, Jan. 30, 2014, 7 pgs.

\* cited by examiner

METHODS AND APPARATUS FOR VACUUM ULTRAVIOLET (VUV) OR SHORTER WAVELENGTH CIRCULAR DICHROISM SPECTROSCOPY

This application claims priority to Provisional Patent Application No. 61/400,153 filed Jul. 22, 2010; the disclosure of which is expressly incorporated herein by reference.

BACKGROUND OF THE INVENTION

The present disclosure relates to the field of polarization spectroscopy. More specifically, it provides a means by which circular dichroism (CD) measurements may be performed in the vacuum ultraviolet (VUV). In one embodiment a highly efficient laboratory-scale VUV CD spectrometer is provided. As used herein, vacuum ultraviolet (VUV) light includes, generally, wavelengths of light that are about 190 nm and less wavelengths.

When light passes through a solution of optically active (e.g. chiral) molecules, left- and right-circularly polarized components traverse the solution with different speeds and are absorbed by the solution to different extents. The differing propagation speeds lead to the effect of optical rotation (OR), which can be probed by measuring the rotation of the polarization plane via optical rotatory dispersion (ORD). Near absorption bands, circular dichroism (CD) spectroscopy measures the differential absorption of left- and right-circularly polarized light by the substance. Both methods have been successfully used to characterize properties of solutions containing optically active molecules. In addition to being sensitive to inherent chirality, ORD and CD are also sensitive to different conformations of complex molecules. As a result, one of the most prolific applications of CD spectroscopy has been the study of the secondary structure of soluble proteins.

Optical rotation and circular dichroism have the same underlying cause, and are related to each other via Kramers-Kronig integration. Defining circular birefringence (CB) as twice the optical rotation, a complex general circular retardation can be defined by:

$$C = CB - iCD \qquad \text{Eqn. 1}$$

where CB and CD are functions of wavelength. The form of Eqn. 1 and the Kramers-Kronig relationship it obeys are familiar from the (isotropic) optical dispersion of materials, n-ik, where n is the material's refractive index and k is the extinction coefficient. That n and k obey the Kramers-Kronig relation implies that the wavelength dependence of the index of refraction is determined by the material's absorption, and vice versa. Similarly, that CB and CD are related via Kramers-Kronig integration implies that complete knowledge of one over all wavelengths or energies determines the other.

Practical experiments, however, occur over finite wavelength ranges and ORD and CD spectroscopy have different advantages, depending on the wavelength range explored. While the ORD spectrum can be determined far from the absorption bands responsible for its effect, the CD spectrum directly probes the bands, and as such, is considered more sensitive and spectrally "compact". In ORD spectroscopy the information associated with a given absorption band is typically spread out over a large energy range. As a result, the ORD spectrum in a given wavelength range contains overlapping contributions from multiple absorption bands. In contrast, with CD spectroscopy the information due to a single absorption band is localized within a smaller energy range, resulting in much less overlap between measured features. If the absorption region is accessible experimentally, CD spectroscopy is typically the preferred technique since it more directly probes the underlying "cause" of the optical activity of the substance being measured.

In the case of soluble proteins, the secondary structure of the molecules results in the optical activity of the solution, and different types of secondary structure, such as alpha-helix, beta sheet, polyproline-II helix, etc. give rise to distinct features in CD spectra. The electronic bands responsible for protein CD largely reside in the ultraviolet. The alpha-helical structures generally involve bands centered at ~222, 208, 192, 175, 160, and 140 nm. Meanwhile, beta sheet structures have weaker bands at ~215, 198, 175, and 168 nm. Variations in beta sheet geometry result in further modifications to CD spectra. The polyprolene-II helix has observed bands near 226 nm and 206 nm, and gives rise to spectra similar to those of proteins previously characterized as "un-ordered". In all cases, other bands may exist but have yet to be observed and/or identified.

The ultraviolet wavelength region may be considered as consisting of two distinct segments: the near-UV region from ~190-400 nm, and the "far-UV" or vacuum ultraviolet (VUV) region below 190 nm. Conventional CD spectrometers are limited in operation down to about 190 nm. The primary motivation to extend CD studies into the VUV lies in the existence of additional absorption bands present at shorter wavelengths. As a consequence of these supplementary features, VUV CD spectra inherently posses increased information content relative to their longer wavelength counterparts. While traditional CD instruments are often limited to determining the amount of alpha-helix structure present in a solution, VUV CD systems are capable of extracting numerous secondary component fractions. In addition, these powerful systems can also provide insight into conformational changes, such as fold state, independent of secondary structure. It is important to note that this information enhancement is not simply due to a "more data is better" argument; the improved capabilities are a direct consequence of the additional absorption bands present in the VUV.

Optical studies in the VUV are difficult to conduct due to the intrinsic absorption of most materials in this region. This phenomenon precludes the simple extension of, or modification to, traditional longer wavelength optical instrumentation to facilitate operation at these energies. To achieve efficient optical performance in the VUV, an instrument must be explicitly designed to do so. Specifically, conventional optical systems are designed to operate in atmospheric conditions and typically lack, among other things, the controlled environment required for operation at these shorter wavelengths. VUV radiation is strongly absorbed by both oxygen and moisture; hence, these species must be maintained at sufficiently low levels in order to permit transmission of VUV photons through instrument optical paths. Attempts to reach shorter wavelengths by simply purging with non-absorbing gases generally yield poor results. Furthermore, transmissive optical components that are otherwise suitable for near-UV or visible wavelength operation, routinely absorb strongly in the VUV. Consequently, reflective elements must instead be employed, greatly restricting design options. As a result, it is comparatively difficult to achieve high optical throughput in VUV optical instrumentation.

With the exception of early work by Johnson (Johnson W. C. (1971). "A circular dichroism spectrometer for the vacuum ultraviolet". Rev. Sci. Instrum. 42(9): 1283-1286), progress towards development of a dedicated, highly efficient VUV-CD instrument has been limited. Today's commercial bench top systems are designed to operate at near-UV and longer wavelengths. Several of these systems offer simplistic purge functionality in an effort to extend capabilities into the VUV. Practically however, poor data quality restricts these instruments to operation at wavelengths above approximately 185 nm.

The most capable VUV CD systems in existence are those integrated into synchrotron radiation (SR) beam lines. The advent of such instruments in the 1980's and 1990's brought about tremendous enhancements in both CD data quality and information content. These improvements however, were largely the result of the remarkable intensity of SR sources, rather than fundamental advancements in instrument designs. As a consequence of these developments, interest in VUV-CD spectroscopy has grown considerably, resulting in the commissioning of several new beam lines and the identification of a myriad of applications for this technology. SR-CD systems are powerful, but the disadvantages are obvious: synchrotron facilities are huge and enormously expensive, making accessibility a severe limitation.

It follows that there would be great benefit in the development of a highly efficient, high throughput laboratory-scale VUV CD spectrometer, which does not require synchrotron radiation. Such an instrument would render high-throughput structural investigations of proteins widely available, thus creating new opportunities to accelerate discoveries in structural proteomics.

SUMMARY OF THE INVENTION

The disclosure herein relates to the field of optical spectroscopy. In one embodiment, a highly efficient bench-top VUV CD spectrometer is provided; the spectrometer suitable for laboratory use or for integration into a beam line at a synchrotron radiation facility.

In one embodiment an spectroscopic circular dichroism instrument is provided. The instrument may comprise a light source which generates a multi-wavelength light beam comprised of light of a plurality of wavelengths; a region of the spectroscopic circular dichroism instrument for the placement of a sample from which a circular dichroism measurement is to be obtained by exposure of a sample to the multi-wavelength light beam; a compensator optically coupled to the multi-wavelength light beam, the compensator providing a circular polarization component to the multi-wavelength light beam light beam; an optical element coupled to the multi-wavelength light beam, the optical element selecting a linearly polarized component of the multi-wavelength light beam; and a detector coupled to the mutli-wavelength light beam to provide a circular dichroism measurement of the sample, the instrument being capable of providing the circular dichroism measurement simulataneously for multiple wavelengths. In a further embodiment, the spectroscopic circular dichroism instrument may have an optical path of the instrument that is configured to allow the multi-wavelength light beam to pass through the compensator and the first optical element after exposure of the sample to the multi-wavelength light beam. In another embodiment, the spectroscopic circular dichroism instrument may have an optical path of the instrument that is configured to allow the multi-wavelength light beam to pass through the compensator and the first optical element before exposure of the sample to the multi-wavelength light beam.

In another embodiment, a spectroscopic CD instrument is provided; the instrument configured so as to enable CD data to be simultaneously obtained for multiple wavelengths. The instrument may be further configured to operate in at least a portion of the VUV wavelength region.

In yet another embodiment, a CD instrument is provided; the instrument configured such that measured data from linearly or circularly anisotropic samples can be analyzed using mathematical expressions to determine the CD signal.

In yet another embodiment, a CD instrument is provided; the instrument configured to employ just a single linear polarizer/analyzer and a single compensator; at least one of said polarizer/analyzer or compensator further configured to rotate.

In yet another embodiment, a CD instrument is provided; the instrument configured to employ a polarizer/analyzer and compensator. The instrument further configured so as to not require alignment of said polarizer/analyzer and compensator, relative to each other and/or the sample, when circularly anisotropic samples lacking linear anisotropic effects are measured.

In yet another embodiment, an optical instrument is provided, the instrument configured to provide sensitivity to all three types of optical anisotropy (circular, linear xy, and linear ±45°) present in a sample. The instrument further configured to employ just a single polarizer/analyzer.

BRIEF DESCRIPTION OF THE DRAWINGS

A more complete understanding of the present concepts and advantages thereof may be acquired by referring to the following description taken in conjunction with the accompanying drawings, in which like reference numbers indicate like features. It is to be noted, however, that the accompanying drawings illustrate only exemplary embodiments of the invention and are therefore not to be considered limiting of its scope, for the invention may admit to other equally effective embodiments.

DESCRIPTION OF THE PREFERRED EMBODIMENTS

Figure 1:
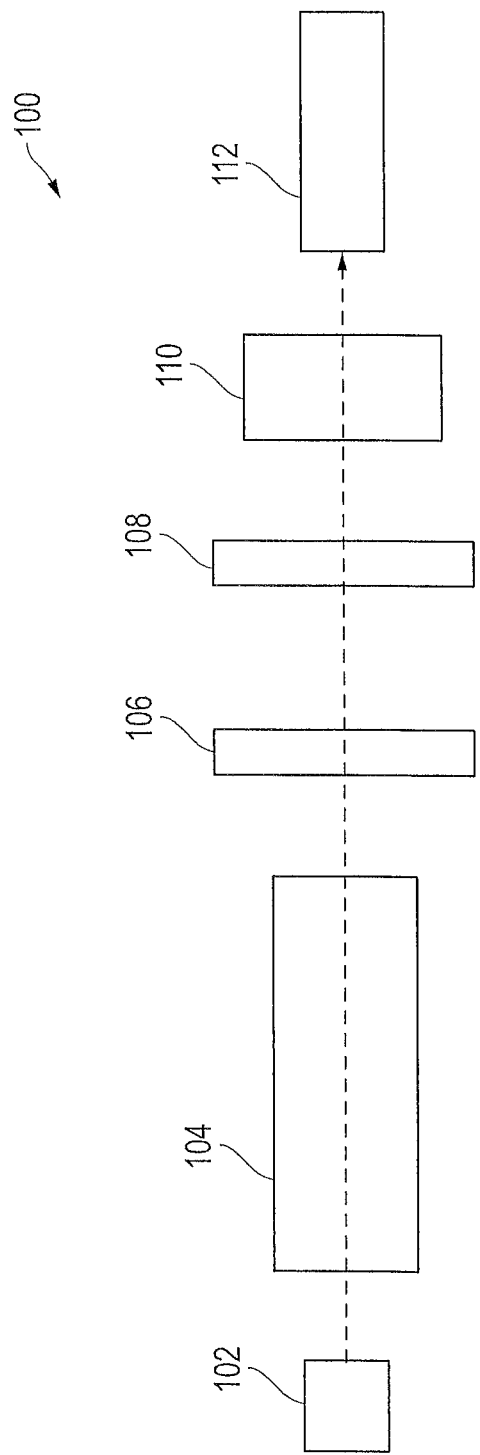
FIG. 1—(Prior Art)—Schematic representation of conventional CD spectrometer.

A typical prior art circular dichroism (CD) spectrometer 100 is presented in FIG. 1. The source 102 light is wavelength-tuned by a monochromator 104 and then passed through a linear polarizer 106 oriented at 45° with respect to the plane of the figure. The linearly polarized light then passes through a photo-elastic modulator (PEM) 108. The PEM is essentially a strain-plate compensator, where the strain condition is oscillated (e.g. at 50 kHz) between +/− quarter-wave conditions so as to transform the linearly polarized light into alternating left- and right-circularly polarized light. The circularly polarized light then passes through the sample cell 110 and is detected by a photomultiplier (PM) tube 112. The PM detector is often used in combination with a lock-in amplifier (not shown). The output from the detector/amplifier is typically analyzed using approximate expressions to infer the circular dichroism of the sample.

One notable disadvantage of the prior art configuration of FIG. 1 is that it is inherently a scanning instrument. This follows since the monochromator is by definition a single-frequency device, the PM is a single element detector sensitive to intensity irrespective of energy, and the quarter-wave condition of the PEM must be adjusted for each wavelength. As a result, data for individual wavelengths must be collected successively, rather than simultaneously.

A step towards a spectroscopic CD instrument design has been proposed by Lewis (Lewis, J. W., Tilton, R. F., Einterz, C. M., Milder, S. J., Kuntz, I. D., Kliger, D. S. (1985). "New technique for measuring circular dichroism changes on a nanosecond time scale. Application to (Cabonmonoxy)myoglobin and (Carbonmonoxy)hemoglobin." *J. Phys. Chem.* 89: 289-294.) The instrument employs a polarizer-compensator-analyzer (PCA) transmission ellipsometer configuration, in conjunction with a broadband source. In operation the initial polarizer axis is oriented horizontally at 0°. The instrument makes two measurements, one with the fast compensator axis at 45° and one with it at −45°, resulting in right and left elliptically polarized light. The resulting signal depends on the sample CD as well as the compensator phase shift. As long as the compensator phase shift is known, the approximate CD signal can be extracted. The benefit of this design is that the compensator phase shift condition need not be adjusted for each wavelength.

Unfortunately however, the instrument of Lewis also incorporates a monochromator and PM detector, and hence, still requires wavelength scanning. In addition, the optical configuration of the system is quite complicated, considering it is only capable of providing the approximate sample CD and does not address CB effects which may also be present. An extension of this design provided by Che (Che D., Goldbeck, R. A., McCauley, S. W., Kliger, D. S. (1994). "Optical analysis of an ellipsometric technique for time-resolved magnetic circular dichroism spectroscopy." *J. Phys. Chem.* 98: 3601-3611) adds an optical rotator that cancels out the sample's circular birefringence. However, the rotator position must also be adjusted for each wavelength in order to achieve this end.

While the system of Che is capable of accounting for the contribution of circular birefringence to the CD signal, it is inherently complicated to operate, owing to the at least four transmissive elements employed (i.e. polarizer, analyzer, compensator and rotator). In fact, in each of these prior art designs there are several optical components whose axes must be aligned with respect to one another in order to perform even the simplest of measurements. The abundance of transmissive elements also gives rise to sample/system coupling issues which obscure data analysis efforts.

A further drawback of prior art CD systems relates to their optically inefficiency, particularly at short wavelengths. Where operation in the vacuum ultra-violet (VUV) is concerned, optical throughput is often limited by absorption in transmissive system elements. Conventional VUV polarizers/analyzers, for example, are notoriously inefficient as a consequence of their considerable thickness. Hence, systems which employ numerous transmissive components generally exhibit poor efficiency at short wavelengths.

In addition to CB and CD, general anisotropic samples may also exhibit linear birefringence and/or dichroism with respect to the optical plane ($LB_1$ and $LD_1$), and/or the 45° plane ($LB_2$ and $LD_2$). The linear birefringence pairs each obey a Kramers-Kronig relation similar to that followed by the circular anisotropy. In cases where only linear effects are present in the sample, it may be desirable to measure linear dichroism and/or birefringence. In general, a sample can exhibit effects of all three birefringence/dichroism pairs, especially where time-dependent processes are concerned. In these cases, it may be desirable to determine linear effects in addition to circular effects. In other cases, it may be desirable to measure circular dichroism, but with minimal error caused by the presence of linear anisotropy effects.

A further drawback of the prior art system shown in FIG. 1 is its lack of sensitivity to the linear ±45° anisotropic effects. Basically, the system is sensitive to only CD and/or one of the linear anisotropy components (X/Y LD). Furthermore, the CD and LD must be extracted from a signal that depends on an infinite series expansion in terms of multiples of the modulator frequency. The instrumentation has to extract the relevant lowest frequencies without being unduly influenced by the higher harmonics. Otherwise, the higher frequencies have to be ignored, which means that the extraction of CD and/or LD is approximate even for pure CD or LD anisotropic samples.

In summary, prior art CD instruments suffer from a myriad of shortcomings, including, but not limited to; single wavelength operation, complicated designs incorporating numerous transmissive elements, tedious alignment requirements, poor VUV optical efficiency, sample/system coupling complications, inexact analysis capabilities, and a lack of sensitivity to certain forms of optical anisotropy.

It follows that there would be great benefit in the development of an instrument which could overcome some, if not all, of these limitations. It would be beneficial if said instrument were truly spectroscopic, providing shorter scan times, faster measurements, and higher throughput than conventional scanning systems. It would be further desirable if said system incorporated fewer transmissive elements, rendering it easier to operate, calibrate, and align, while still providing sensitivity to all forms of optical anisotropy. It would be of yet further benefit if said system was optically efficient in the VUV and could be used to collect high quality VUV CD spectra without use of a synchrotron radiation source.

Figure 2:
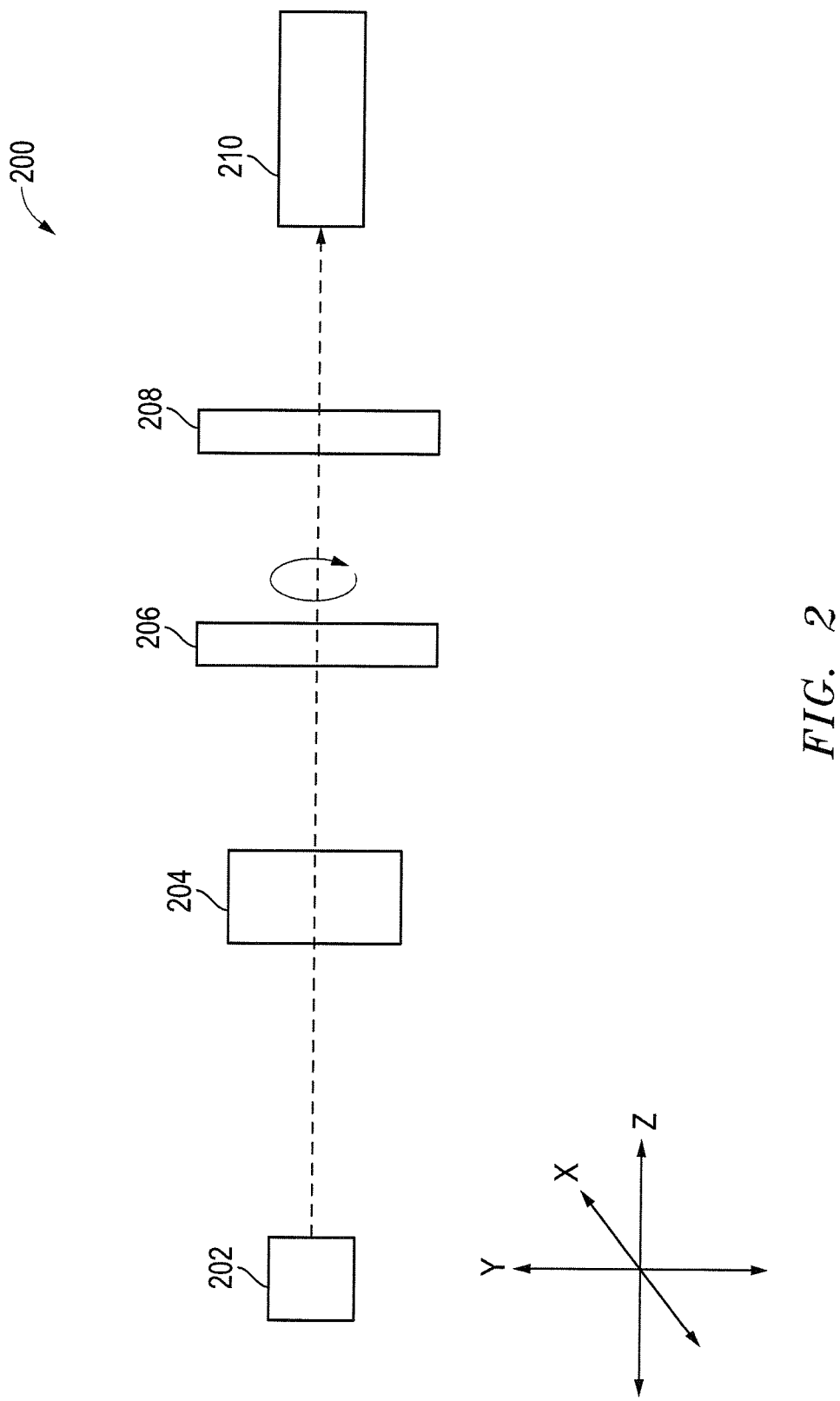
FIG. 2—Schematic representation of an embodiment configured such that light encounters the sample before the compensator and analyzer.
Figure 3:
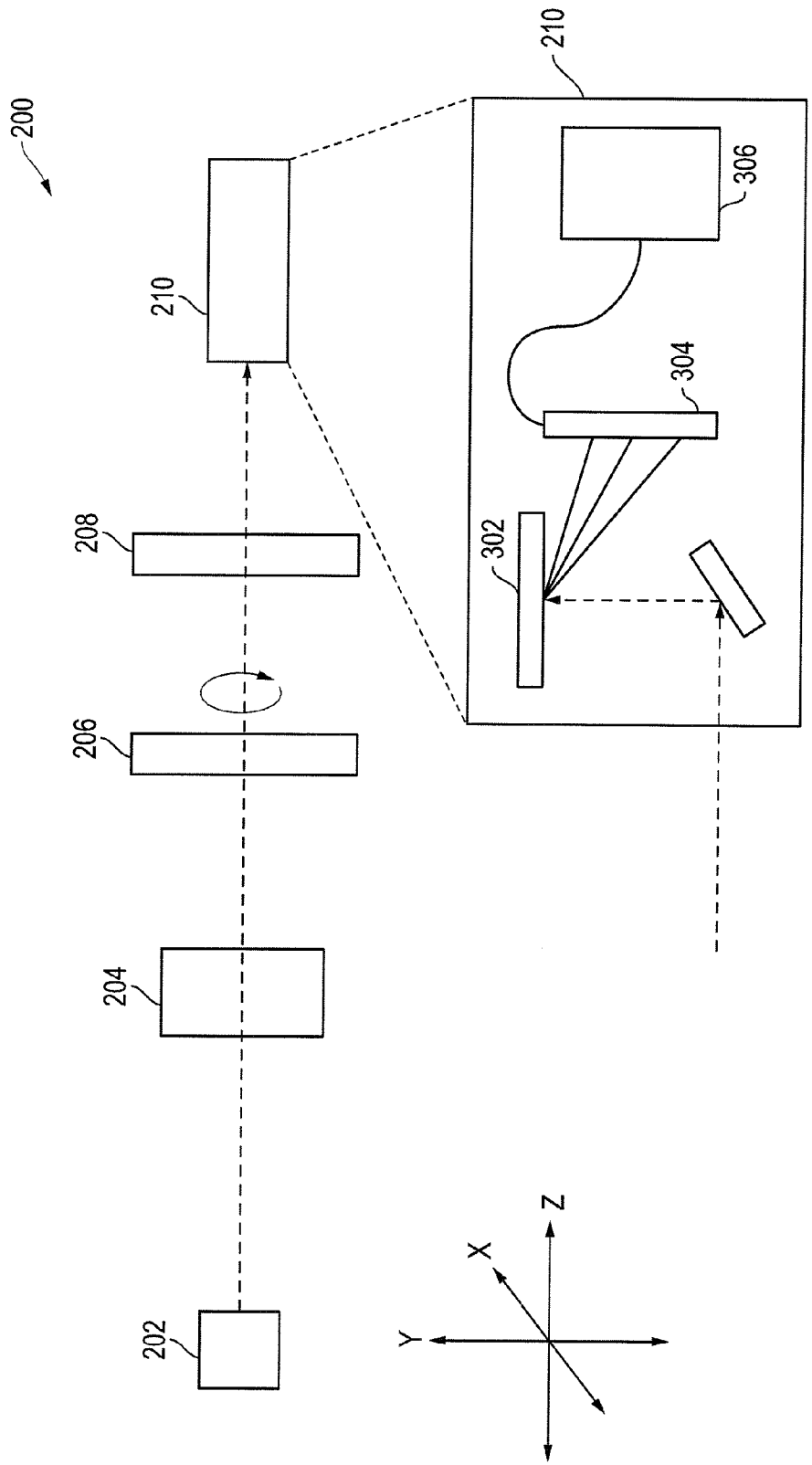
FIG. 3—Schematic representation of an embodiment with further details of the spectrometer-detector. The embodiment is configured such that light encounters the sample before the compensator and analyzer.

A schematic representation of an instrument 200 which embodies these desirable traits is presented in FIGS. 2 and 3. The system consists of a broadband source 202, followed by the sample 204, a compensator 206, which in one embodiment is continuously rotated during measurement, an analyzer 208 (which may be mechanism which can change the light polarization), and finally a spectrometer-detector 210. The compensator imparts a circular polarization component into the beam. The spectrometer-detector (shown in greater detail in FIG. 3) is comprised of both a dispersive/diffractive element 302 and a multi-element array detector 304, like a photodiode array (PDA) or charge coupled device (CCD).

The broadband light from the optical system is spatially separated by the dispersive/diffractive element, such that light of different wavelengths illuminates the detector array at different locations. The electronics 306 report an electrical signal, intensity, or photon count, versus array position to a computer. In contrast with the prior art configuration of FIG. 1, the CD system of FIG. 3 is truly spectroscopic and does not require wavelength scanning.

During operation, the compensator may be rotated with a fixed frequency. The detected signal will consist of intensity as a function of compensator rotation angle, which can be Fourier analyzed to extract sample parameters. A preferred means of determining the content of the detected signal is to perform an analysis of the optical system using Mueller Calculus. Each optical element, including the sample, is represented by a 4×4 matrix that transforms an input Stokes vector, which is composed of four elements that represent the polarization state of the incident light. The elements of the Stokes vector consist of the total light intensity, $S_0$, the difference of intensities polarized along the horizontal (x-axis in FIGS. 2 and 3) and vertical axes, $S_1$, the difference of intensities polarized along +/−45° with respect to the horizontal plane, $S_2$, and the difference of intensities of right and left circularly polarized light, $S_3$. The Stokes vector for horizontally polarized light is $(S_0, S_1, S_2, S_3)^T=(1,1,0,0)^T$, while that of left-circularly polarized light is $(1,0,0,-1)^T$, and so on.

An optical element Mueller matrix transforms an input Stokes vector into another state, represented by the output Stokes vector. The initial input vector is usually assumed to consist of completely unpolarized light, or $(1,0,0,0)^T$. Each Mueller matrix is applied to the input light in the order it is encountered, which has the effect of inducing additional polarization components, as well as coupling in optical parameters, such as polarizer efficiency and compensator phase shift angle. The (normalized) output at the detector is the $S_0$ element of the final Stokes vector.

The Mueller matrices for standard optical elements can be found in ellipsometry texts (e.g. Fujiwara, H. (2007). "*Spectroscopic Ellipsometry: Principles and Applications.*" John Wiley & Sons Ltd.) The Mueller matrix for a sample exhibiting multiple types of anisotropies can be found in the literature (Che et al. 1994, Schellman, J., Jensen, H. P. (1987). "Optical spectroscopy of oriented molecules." *Chem. Rev.* 87: 1359-1399). Note that the elements of the Stokes vector as defined above are consistent with Fujiwara (Fujiwara 2007) and Che (Che et al. 1994). Schellman (Schellman et al. 1987) uses a different ordering, where $S_3$ corresponds to x/y polarization (with respect to the optics plane), $S_1$ to +/−45° polarization, and $S_2$ to circular polarization. Either definition is fine, but the elements of the Mueller matrix must be consistent with those of the Stokes ordering. This disclosure uses an ordering consistent with Fujiwara and Che, and any references to Mueller matrix elements from Schellman are re-ordered so as to be consistent with this convention.

While a general sample might well exhibit all six anisotropic effects, some common cases involve smaller subsets of these parameters. In a case where the sample consists of a well-relaxed, homogenous solution, and where no external perturbations to the sample solution are introduced, linear anisotropies tend to vanish, leaving only circular anisotropic effects, CB and CD. The sample Mueller matrix is then given by $$M_S = e^{-A} \cdot \begin{bmatrix} \cosh CD & 0 & 0 & \sinh CD \\ 0 & \cos CB & \sin CB & 0 \\ 0 & -\sin CB & \cos CB & 0 \\ \sinh CD & 0 & 0 & \cosh CD \end{bmatrix}, \quad \text{Eqn. 2}$$

where A is the mean absorbance. The Mueller matrix for a vertical polarizer/analyzer is given by $$M_{VP} = \frac{1}{2} \cdot \begin{bmatrix} 1 & -1 & 0 & 0 \\ -1 & 1 & 0 & 0 \\ 0 & 0 & 0 & 0 \\ 0 & 0 & 0 & 0 \end{bmatrix}, \quad \text{Eqn. 3}$$

and the matrix for a compensator of phase shift δ with fast axis at an angle β is $$M_C(\beta, \delta) = \quad \text{Eqn. 4}$$
$$\begin{bmatrix} 1 & 0 & 0 & 0 \\ 0 & \cos^2 2\beta + \sin^2 2\beta \cos\delta & \sin 2\beta \cos 2\beta (1-\cos\delta) & -\sin 2\beta \sin\delta \\ 0 & \sin 2\beta \cos 2\beta (1-\cos\delta) & \sin^2 2\beta + \cos^2 2\beta \cos\delta & \cos 2\beta \sin\delta \\ 0 & \sin 2\beta \sin\delta & -\cos 2\beta \sin\delta & \cos\delta \end{bmatrix}$$

Eq. 4 can be readily derived by applying a rotation matrix of angle β to the Mueller matrix for a compensator with horizontal fast axis according to $M_C(\beta,\delta)=R(-\beta)M_C(0,\delta)R(\beta)$.

Starting with the input Stokes vector, $S_i=(1,0,0,0)^T$, the output vector for the embodiment of FIG. 3 is computed from $$S_f = M_{VP} M_C(\beta,\delta) M_S S_i. \quad \text{Eqn. 5}$$

The normalized detector intensity is given by the $S_0$ element of $S_f$, which is $$I_D(t,\delta) = A_0 + A_1 \sin 2\omega t$$

where β=ωt for a compensator rotated at a constant angular frequency, ω, and $$A_0 = \frac{1}{2} e^{-A} \cosh CD \quad \text{Eqn. 6}$$

$$A_1 = \frac{1}{2} e^{-A} \sinh CD \sin\delta$$

The ac and dc components can be extracted from the time-dependent signal (e.g., using Fourier analysis), and their ratio is $$\frac{A_1}{A_0} = \frac{\sin\delta \sinh CD}{\cosh CD} = \sin\delta \tanh CD. \quad \text{Eqn. 7}$$

Equation 7 is solved for the CD, which is uniquely determined as long as δ is known either from the compensator design or a calibration procedure. While generally not necessary when using modern computers/programming languages, for typical CD values that are $10^{-3}$-$10^{-5}$ of the total absorption, the approximations $\cos hCD \approx 1$, $\sin hCD \approx \tan hCD \approx CD$ can also be used. In a typical measurement using an array detector, the measurement consists of an intensity signal like Eqn. 6 (and a value for $A_1/A_0$) for each of the array pixels/elements, corresponding to different wavelengths. The result of the measurement is a spectrum of CD versus wavelength. The appropriate value of $\delta$ for each wavelength is used in Eqn. 7.

A second special case occurs when only linear effects are present in the sample. In this case, the sample Mueller matrix is given by:

$$M_S = e^{-A} \cdot \begin{bmatrix} \cosh LD & -\sinh LD & 0 & 0 \\ -\sinh LD & \cosh LD & 0 & 0 \\ 0 & 0 & \cos LB & -\sin LB \\ 0 & 0 & \sin LB & \cos LB \end{bmatrix} \quad \text{Eqn. 8}$$

when the sample is uniaxial with the fast axis of the birefringence aligned along the x direction (horizontal laboratory axis). This time the normalized detected intensity is given by:

$$I_D(t, \delta) = A_0 + A_2 \cos 4\omega t \quad \text{Eqn. 9}$$

where $$A_0 = \frac{1}{2} e^{-A} \left[ \cosh LD + \frac{1}{2}(1 + \cos\delta)\sinh LD \right]$$

$$A_2 = \frac{1}{4} e^{-A}(1 + \cos\delta)\sinh LD.$$

The ac signal is twice the frequency as before, and the ratio of ac to dc components is $$\frac{A_2}{A_0} = \frac{(1 - \cos\delta)\sinh LD}{2\left[\cosh LD + \frac{1}{2}(1 + \cos\delta)\sinh LD\right]} \quad \text{Eqn. 10}$$

$$\approx \frac{1}{2}(1 - \cos\delta)LD$$

when the LD is small. Eqn. 10 can also be solved directly for tan h(LD) by factoring cos h(LD) out of the denominator as shown in Eqn. 10A.

$$\tanh LD = \frac{2A_2/A_0}{(1 - \cos\delta) - (1 + \cos\delta)A_2/A_0} \quad \text{Eqn. 10A}$$

A slightly more convenient set of relations results when the analyzer in FIG. 3 is oriented at ±45° with respect to the x axis. The analyzer Mueller matrix for ±45° orientation is $$M_{\pm 45} = \frac{1}{2} \cdot \begin{bmatrix} 1 & 0 & \pm 1 & 0 \\ 0 & 0 & 0 & 0 \\ \pm 1 & 0 & 1 & 0 \\ 0 & 0 & 0 & 0 \end{bmatrix} \quad \text{Eqn. 11}$$

For a 45° analyzer and the compensator rotated at angular frequency $\omega$, the normalized intensity at the detector is $$I_D(t, \delta) = A_0 + A_1 \cos 2\omega t \quad \text{Eqn. 12}$$

with $$A_0 = \frac{1}{2} e^{-A} \cosh CD$$

$$A_1 = \frac{1}{2} e^{-A} \sin\delta \sinh CD$$

for a sample exhibiting only circular effects (Eqn. 2). The ratio of ac to dc signals is again $$\frac{A_1}{A_0} = \sin\delta \tanh CD. \quad \text{Eqn. 13}$$

For a sample exhibiting only linear effects (Eqn. 8), the normalized intensity is $$I_D(t, \delta) = A_0 + A_2 \sin 4\omega t \quad \text{Eqn. 14}$$

with $$A_0 = \frac{1}{2} e^{-A} \cosh LD$$

$$A_2 = -\frac{1}{4} e^{-A}(1 - \cos\delta)\sinh LD.$$

and the ratio of ac to dc signals is $$\frac{A_2}{A_0} = \frac{1}{2}(\cos\delta - 1)\tanh LD. \quad \text{Eqn. 15}$$

Using the embodiment shown in FIG. 3, when the sample exhibits only circular anisotropies (CB and CD), the result of the measurement is Eqn. 7. When only linear anisotropies are present, the result of the measurement is Eqn. 10. The analyzer can also be rotated to 45° from the x axis, which results in Eqn. 13 for circular anisotropy and Eqn. 15 for linear anisotropy. In either case, a CD signal is extracted from the dc and $2\omega$ components of the detected signal, while LD is extracted from the dc and $4\omega$ components, as long as the compensator phase shift, $\delta$, is known.

Note that since the compensator is continuously rotated during the measurement, the orientation of the optics plane is determined entirely by the analyzer axis, with horizontal polarization corresponding to alignment with the x axis, and vertical polarization to the y axis. Therefore, when measuring linear anisotropy, the fast axis of the sample can be oriented to correspond to the optical x axis by rotating either the sample or analyzer. When the analyzer axis is aligned at 90° from the sample fast axis, Eqns. 7 and 10 result. When the analyzer axis is oriented at 45° from the sample fast axis, Eqns. 13 and 15 result. That Eqns. 7 and 13 are identical follows due to the fact that the analyzer orientation should not matter when only circular anisotropy is present in the sample. Comparison of Eqns. 10 and 15 show that orienting the analyzer at 45° with respect to the sample linear birefringence fast axis results in a slightly more convenient relation to solve for the linear dichroism. We note that other analyzer orientations will also work; in particular, horizontal or −45° analyzer orientation will result in similar information about the sample, with equations slightly modified from those shown.

In the case of a sample exhibiting only circular anisotropy, an advantage of the present techniques over the prior art is that none of the optical component axes need be aligned, since the compensator is continuously rotated and the result is independent of the analyzer axis (Eqns. 7 and 13). However, the analysis of the signal must take into account an additional phase, $\phi$, that is related to the initial angle between the compensator fast axis and the analyzer axis. In this case, the output Stokes vector is determined from $$S_f = M_{HP} R(\phi) M_C(\beta,\delta) M_S S_i \qquad \text{Eqn. 16}$$

where the horizontal polarizer matrix is $$M_{HP} = \frac{1}{2} \cdot \begin{bmatrix} 1 & 1 & 0 & 0 \\ 1 & 1 & 0 & 0 \\ 0 & 0 & 0 & 0 \\ 0 & 0 & 0 & 0 \end{bmatrix} \qquad \text{Eqn. 17}$$

and the rotation matrix is $$R(\phi) = \begin{bmatrix} 1 & 0 & 0 & 0 \\ 0 & \cos 2\phi & \sin 2\phi & 0 \\ 0 & -\sin 2\phi & \cos 2\phi & 0 \\ 0 & 0 & 0 & 1 \end{bmatrix}, \qquad \text{Eqn. 18}$$

where $\phi$ is measured from the horizontal axis. The normalized detector intensity is then $$I_D(t,\delta) = A_0 + A_1 \cos 2\omega t + A_2 \sin 2\omega t \qquad \text{Eqn. 19}$$

with $$A_0 = \frac{1}{2} e^{-A} \cosh CD$$

$$A_1 = \frac{1}{2} e^{-A} \sin 2\phi \sin\delta \sinh CD$$

$$A_2 = -\frac{1}{2} e^{-A} \cos 2\phi \sin\delta \sinh CD$$

The dc, $\cos 2\omega t$, and $\sin 2\omega t$ coefficients can be extracted, and $$\frac{\sqrt{A_1^2 + A_2^2}}{A_0} = \sin\delta \tanh CD. \qquad \text{Eqn. 20}$$

Eqn. 20 can be solved for the CD, and $\phi$ does not need to be known. Therefore the initial compensator axis does not need to be aligned with respect to the analyzer axis. Furthermore, the analyzer axis was chosen to be horizontal with respect to the laboratory frame in the above derivation simply for the sake of convenience in the calculation. The final result Eqn. 20 clearly cannot depend on the analyzer orientation with respect to the laboratory frame, so when only circular anisotropy is present in the sample, none of the optical axes need to be aligned with respect to any particular plane.

Eqns. 7, 10, 13, 15, and/or 20 can be used as approximations for the sample CD and LD if the sample anisotropy is mostly circular or mostly linear. In one embodiment, a measurement is performed with the analyzer in the 45° position (with respect to the sample linear axis) and rotating the compensator with angular frequency $\omega$. The dc and $2\omega$ components can be used to extract the CD from Eqn. 13, while the LD can be extracted from the dc and $4\omega$ component via Eqn. 15.

When circular and linear anisotropy are both present to significant extents, the approximations can be made more accurate. A general sample matrix where no assumptions are made about sample anisotropies can be represented by $$M_S = \begin{bmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{bmatrix}. \qquad \text{Eqn. 21}$$

With un-polarized input $(S_i^T = (1,0,0,0)^T)$, the Stokes vector after the sample is given by $$M_S S_i = \begin{pmatrix} M_{00} \\ M_{10} \\ M_{20} \\ M_{30} \end{pmatrix}. \qquad \text{Eqn. 22}$$

Basically, un-polarized input is sensitive to the first column of the sample Mueller matrix. In the embodiment of FIG. 3, the light then passes through a compensator (Eqn. 4) and an analyzer (Eqn. 3 for a vertical analyzer). The signal that results when the compensator is rotated with angular frequency $\omega(\beta=\omega t)$ is $$I_D(t,\delta) = A_0 + A_1 \sin 2\omega t + A_2 \cos 4\omega t + A_3 \sin 4\omega t \qquad \text{Eqn. 23}$$

where $$A_0 = \frac{1}{2} M_{00} - \frac{1}{4}(1+\cos\delta) \cdot M_{10}$$

$$A_1 = \frac{1}{2} \sin\delta \cdot M_{30}$$

$$A_2 = \frac{1}{4}(\cos\delta - 1) \cdot M_{10}$$

$$A_3 = \frac{1}{4}(\cos\delta - 1) \cdot M_{20}$$

The coefficients can be extracted by Fourier analysis:

$$\frac{A_1}{A_0} = \frac{\sin\delta \cdot M_{30}/M_{00}}{1 - \frac{1}{2}(1+\cos\delta) M_{10}/M_{00}} \qquad \text{Eqn. 24}$$

$$\frac{A_2}{A_0} = \frac{\frac{1}{2}(\cos\delta - 1) \cdot M_{10}/M_{00}}{1 - \frac{1}{2}(1+\cos\delta) M_{10}/M_{00}}$$

$$\frac{A_3}{A_0} = \frac{\frac{1}{2}(\cos\delta - 1) \cdot M_{20}/M_{00}}{1 - \frac{1}{2}(1+\cos\delta) M_{10}/M_{00}}.$$

Since the $A_2/A_0$ ratio depends only on $M_{10}/M_{00}$, it can be solved for $M_{10}/M_{00}$ and the result can be used in the other two ratios, which are solved for $M_{30}/M_{00}$ and $M_{20}/M_{00}$. Therefore, the configuration of FIG. 3 can be used to measure all three ratios $M_{10}/M_{00}$, $M_{20}/M_{00}$, and $M_{30}/M_{00}$ as long as the compensator phase shift δ is known. By contrast, the prior art CD spectrometer shown in FIG. 1 is only sensitive to $M_{01}/M_{00}$ and $M_{03}/M_{00}$.

In the general case six anisotropic components (CD, CB, $LD_1$, $LB_1$, $LD_2$, and $LB_2$) can occur together in the sample, arising from the three types of anisotropy (circular, linear xy, and linear ±45°). Complicating matters is the fact that the effects of the different types of anisotropy do not commute. As a result, most representations of the general sample matrix express the individual matrix elements as series expansions:

$$M_{00} = \frac{e^{-A}}{2}(2 + CD^2 + LD_1^2 + LD_2^2 + \ldots)$$ Eqn. 25

$$M_{10} = \frac{e^{-A}}{2}(-2LD_1 + CD \cdot LB_2 - CB \cdot LD_2 + \ldots)$$

$$M_{20} = \frac{e^{-A}}{2}(-2LD_2 + CB \cdot LD_1 - CD \cdot LB_1 + \ldots)$$

$$M_{30} = \frac{e^{-A}}{2}(2CD + LD_1 \cdot LB_2 - LD_2 \cdot LB_1 + \ldots).$$

In practice, the matrix elements are truncated after second- or third-order terms. Terms up to second order are shown explicitly in Eqn. 25.

The $M_{00}$ element is just the total intensity transmitted through the sample. This could be obtained via a transmittance measurement or the ratio of intensity with sample present to the intensity without the sample, although this additional measurement is usually not necessary when measuring circular or linear dichroism. Each of the remaining elements is dominated by one of the dichroism terms: $LD_1$ for $M_{10}$, $LD_2$ for $M_{20}$, and CD for $M_{30}$. Each element also has a second-order term that can be thought of as an error term; the presence of two types of anisotropy results in a contribution to the signal for the third type. So, for example, the presence of both xy and ±45° linear anisotropies contributes an apparent CD signal via $M_{30}$. Similarly, the presence of circular and ±45° anisotropies results in a contribution to the apparent xy linear dichroism via $M_{10}$.

In a case where circular anisotropy and one linear component exist, the analyzer (or sample) can be oriented such that the birefringence axis corresponds to the x axis (in practice, sample birefringence and analyzer axis are at right angles for a vertical analyzer in FIG. 3). The linear anisotropy then corresponds to $LB_1$ and $LD_1$, and $LB_2=LD_2=0$. The error terms vanish from $M_{10}$ and $M_{30}$, and the linear and circular dichroism can be extracted from $A_1/A_0$ and $A_2/A_0$ of Eqn. 24. Note that in the usual case of LD>>CD and CD<<1, the Mueller matrix ratios reduce to $$\frac{M_{10}}{M_{00}} \approx \frac{-LD_1}{1 + \frac{1}{2}LD_1^2}$$ Eqn. 26 and $$\frac{M_{30}}{M_{00}} \approx \frac{CD}{1 + \frac{1}{2}LD_1^2}.$$ Eqn. 27

When the sample anisotropy obeys these conditions, Eqns. 24, 26, and 27 suggest that it is possible to ignore the circular anisotropy contribution to $M_{00}$, and use the second ratio in Eqn. 24 along with Eqn. 26 to extract the LD from the sin 4ω component. The result can be used along with the 2ω signal to extract the CD via Eqn. 27 and the first ratio in Eqn. 24.

If both LD<<1 and CD<<1, also a common case, then both the linear and circular anisotropy contributions to $M_{00}$ can be ignored, and we have $(M_{10}/M_{00}) \cong -LD_1$ and $(M_{30}/M_{00}) \cong CD$.

Finally, it is noted that if there are only circular or linear effects present, so that the sample matrix is represented by Eqn. 2 for circular anisotropy or Eqn. 8 for linear anisotropy, application of Eqns. 23 and 24 results in the same equations as derived previously for those special cases. In particular, for circular anisotropy only, we have $M_{30}/M_{00}=\tan h(CD)$, $M_{10}/M_{00}=M_{20}/M_{00}=0$. For linear anisotropy only, $M_{10}/M_{00}=-\tan h(LD)$, $M_{20}/M_{00}=M_{30}/M_{00}=0$.

The analyzer could also be oriented at 45° with respect to the sample birefringence axis, resulting in the normalized output $$I_D(t, \delta) = A_0 + A_1\cos2\omega t + A_2\cos4\omega t + A_3\sin4\omega t,$$ Eqn. 28 where $$A_0 = \frac{1}{2}M_{00} + \frac{1}{4}(1 + \cos\delta) \cdot M_{20}$$

$$A_1 = \frac{1}{2}\sin\delta \cdot M_{30}$$

$$A_2 = \frac{1}{4}(\cos\delta - 1) \cdot M_{20}$$

$$A_3 = \frac{1}{4}(1 - \cos\delta) \cdot M_{10}$$

The coefficients can be extracted by Fourier analysis:

$$\frac{A_1}{A_0} = \frac{\sin\delta \cdot M_{30}/M_{00}}{1 + \frac{1}{2}(1 + \cos\delta)M_{20}/M_{00}}$$ Eqn. 29

$$\frac{A_2}{A_0} = \frac{\frac{1}{2}(\cos\delta - 1) \cdot M_{20}/M_{00}}{1 + \frac{1}{2}(1 + \cos\delta)M_{20}/M_{00}}$$

$$\frac{A_3}{A_0} = \frac{\frac{1}{2}(1 - \cos\delta) \cdot M_{10}/M_{00}}{1 + \frac{1}{2}(1 + \cos\delta)M_{20}/M_{00}}$$

In this case, the ratio denominators contain the $M_{20}/M_{00}$ term, which in the case of circular anisotropy and a single linear anisotropy type ($LD_2=LB_2=0$) consists of only the error term $CD \cdot LB_1 - CB \cdot LD_1$. This configuration may be advantageous when the error term is small, but at any rate the error term can be determined from $A_2/A_0$. This time, the CD and $LD_1$ are contained in the $A_1/A_0$ and $A_3/A_0$ components. The analyzer in the present embodiment can also be oriented horizontally or at −45° with respect to the sample birefringence axis, with slight modifications to the output equations. Again, Eqns. 28 and 29 reduce to previously derived equations for samples exhibiting circular anisotropy only or linear anisotropy only.

Figure 4:
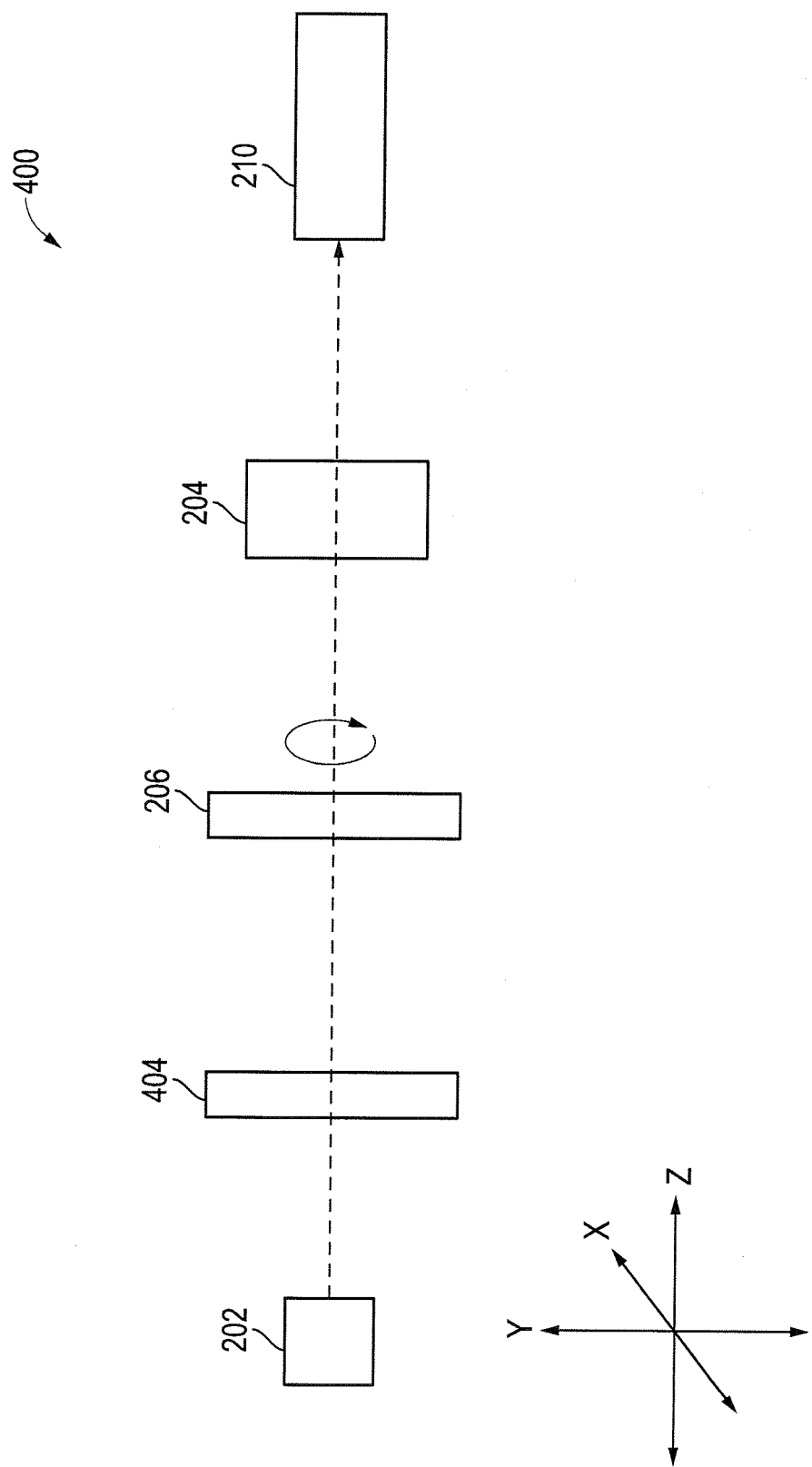
FIG. 4—Schematic representation of another embodiment that is configured such that light encounters the sample after the polarizer and compensator.

An alternate embodiment of the present disclosure is illustrated in FIG. 4. In this configuration the polarizer 404 and compensator 206 are placed before the sample 204, rather than after. Performing a measurement with polarizer and compensator before the sample results in sensitivity to the first row of the Mueller matrix (as opposed to the first column as before):

$$M_{00} = \frac{e^{-A}}{2}(2 + CD^2 + LD_1^2 + LD_2^2 + \dots)$$ Eqn. 30

$$M_{01} = \frac{e^{-A}}{2}(-2LD_1 + CB \cdot LD_2 - CD \cdot LB_2 + \dots)$$

$$M_{02} = \frac{e^{-A}}{2}(-2LD_2 + CD \cdot LB_1 - CB \cdot LD_1 + \dots)$$

$$M_{03} = \frac{e^{-A}}{2}(2CD + LD_2 \cdot LB_1 - LD_1 \cdot LB_2 + \dots)$$

Comparison of Eqns. 30 and 25 shows that the error terms are of equal magnitude, but opposite in sign, so measurements that determine both the first row and first column of the sample Mueller matrix can be used to cancel out the error terms. For example, $M_{30}+M_{03}=2e^{-A} \cdot CD$, and so on. Measurement of the first row and column of the sample matrix can be achieved by performing a measurement using the configuration of FIG. 3 along with a separate measurement using the configuration in FIG. 4.

Further comparison of the systems in FIGS. 3 and 4 reveal that they are both sensitive to very similar sample information. For example, when the sample matrix is given by Eq. 2, the embodiment of FIG. 4 also results in Eq. 7. However, depending on the type of spectrometer-detector used, the polarization efficiency of the spectrometer-detector may need to be pre-characterized since the detected light now has a variable polarization state. When using the embodiment of FIG. 3, the signal does not depend on spectrometer-detector polarization efficiency, since the polarization state of the signal is fixed by the analyzer. Hence, the embodiment of FIG. 3 may be preferred if detector polarization sensitivity is of concern.

Alternatively, polarization-dependence may be eliminated from the source and/or detection sides of the systems through introduction of one or more depolarizers. One way to make a depolarizer is to construct a wedge of birefringent material. The amount of material traversed by the light incident on the depolarizer varies across the beam path, which means that the induced phase difference also varies across the beam diameter. Thus, the emergent beam is effectively randomly polarized. For operation in the VUV, a wedge depolarizer constructed of birefringent $MgF_2$ may be employed. Any of the embodiments of the present invention may be modified by incorporating a depolarizer immediately after the source and/or before the spectrometer-detector.

When all three types of anisotropy are present in a sample, it may be desirable to perform additional measurements including other optical elements. Hence, further modifications to the disclosed techniques include the ability to readily insert or remove various optical components, and in particular, the ability to perform measurements with either or both a rotating polarizer and rotating compensator, and with a rotating compensator either before and/or after the sample, or both. While resulting in more complicated detection signals and measurement procedures, such an approach explores additional elements of the sample Mueller matrix, allowing a determination of more simultaneously occurring anisotropies.

Figure 5:
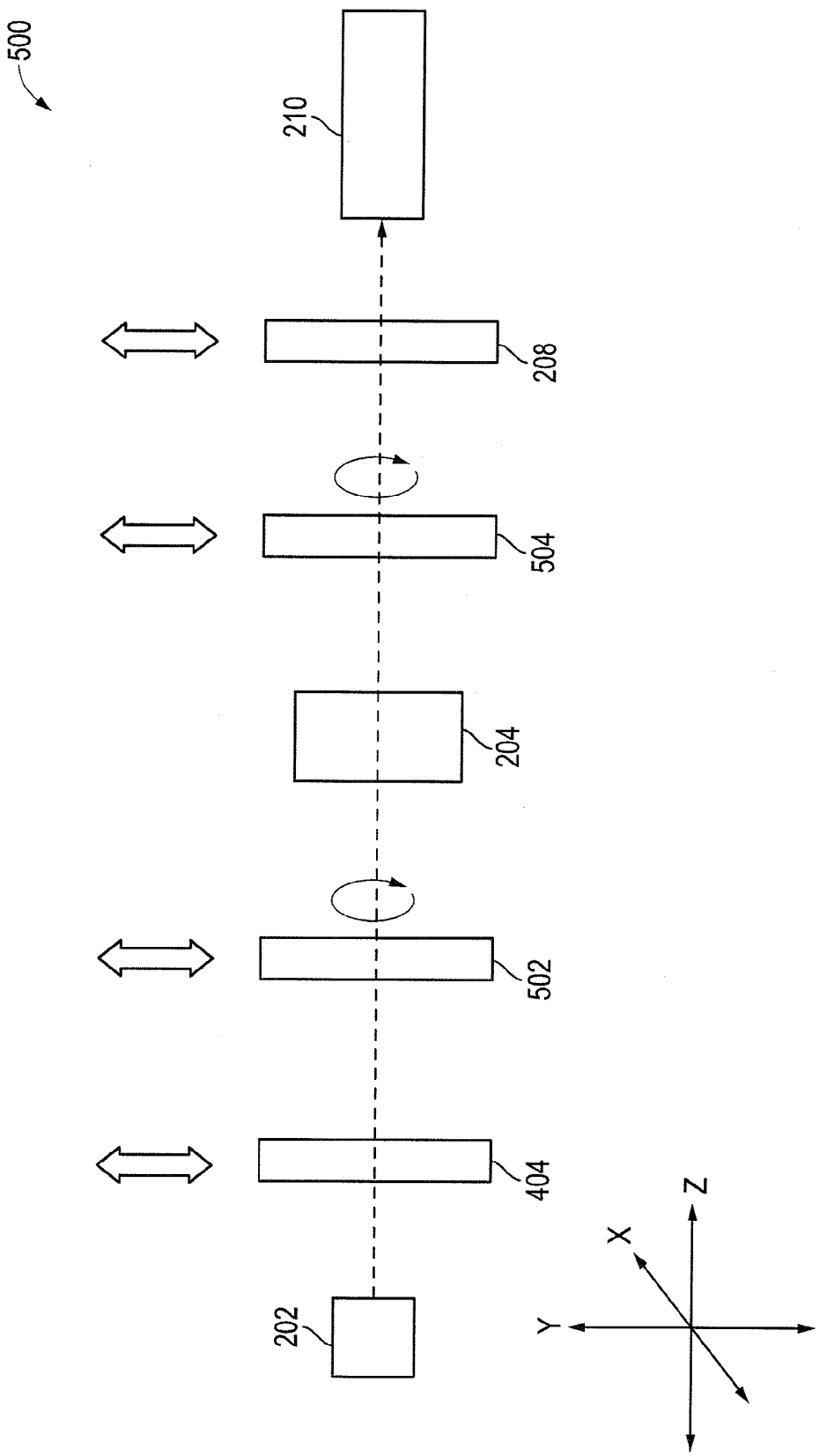
FIG. 5—Schematic representation of a versatile embodiment with polarizers, analyzers and compensators configurable such that they can be inserted into or removed from the beam path.

A very general configuration and one that is capable of independently obtaining all components of the sample Mueller matrix is shown in the embodiment 500 of FIG. 5. In this dual-rotating compensator configuration, the two compensators 502 and 504 are rotated simultaneously, but at different frequencies. Each of the optical elements (polarizer 404, analyzer 208, sample 204, first compensator 502, and second compensator 504) can be inserted into or removed from the optical path, depending on the sample being measured. In addition, each of the elements can also be independently rotated during measurement, if desired.

The embodiment of FIG. 5 can be converted to the embodiment of FIG. 3 by removing the initial polarizer and compensator, and rotating the remaining compensator during operation. The embodiment of FIG. 5 can be converted into a transmission rotating compensator ellipsometer by removing the second compensator and operating in a rotating compensator configuration with polarizer and analyzer fixed. Alternatively, the embodiment of FIG. 5 can be converted into the embodiment of FIG. 4 by removing the final polarizer and compensator and rotating the first compensator during operation. Thus, in one embodiment, the embodiment of FIG. 5 may have removable elements which allow for a selectable configuration of the system.

The choice of which components to include and/or rotate during data collection will depend on the types of anisotropy (linear, circular, or both) expected in the sample. Accordingly, some embodiments will simply extract the CD or LD signal from the sample when other types of anisotropy are not present. Still other embodiments will extract the CD signal when linear anisotropies are also present in the sample. Such embodiments are particularly useful for time-dependent studies of solutions that have not yet reached equilibrium. Still other embodiments will extract all 6 anisotropy components ($LB_1$, $LD_1$, $LB_2$, $LD_2$, CB, and CD) from an arbitrary system.

The above analysis (Eqn. 7, etc.) shows that while the detected signal contains the desired sample anisotropy information, it can also include terms that depend on the optical components themselves. In particular, the trade-off for using a chromatic compensator is that the compensator phase shift condition has to be known in advance. This is accomplished through a calibration procedure, often done using a straight-through configuration (with sample removed) or using a known standard. When done using a straight-through configuration especially, the calibration procedure is basically an ellipsometric characterization of the optic element itself. For a compensator, the result is a spectrum of induced phase shift $\delta$, versus wavelength, which can then be used in subsequent measurements with unknown samples in place (e.g. in Eqn. 7).

The compensator phase shift can be back-calculated using measurements of samples or optics having known CD and/or LD spectra. For example, an optic having known LD can be measured using the embodiment shown in FIG. 3, with the known optic in place of the sample. The compensator phase shift can be extracted from Eqn. 10 or Eqn. 15, depending on how the analyzer axis is set. This procedure actually determines $\cos \delta$, but the approximate value of $\delta$ at each wavelength is usually known from the compensator design material and thickness, so the value of $\cos \delta$ is enough to determine $\delta$ or $\sin \delta$ unambiguously. Alternatively, a sample or optic having known CD can be used to extract $\sin \delta$.

The contribution of cell strain on sample measurements can also be determined using the FIG. 3 embodiment. In particular, the presence of a $4\omega$ signal when measuring an empty sample cell (or anything else, for that matter) is an indication of linear anisotropy, while the presence of a $2\omega$ signal indicates circular anisotropy.

Other wavelength-dependent optical effects, such as polarization extinction ratio, may also need to be pre-characterized via a calibration procedure. Where appropriate, some of the many procedures developed over the years for characterizing the optical components used in ellipsometers (e.g. Fujiwara 2007; Lee J., Rovira, P. I., An, I., Collins, R. W. (2001)

"Alignment and calibration of the MgF$_2$ biplate compensator for applications in rotating-compensator multichannel ellipsometry." *J. Opt. Soc. Am. A* 18(8): 1980-1985; Collins R. W. (1990). "Automatic rotating element ellipsometers: Calibration, operation, and real-time applications." *Rev. Sci. Instrum.* 61(8): 2029-2062; de Nijs J. M. M., Holtslag, A. H. M, Hoeksta, A., and van Silfhout, A. (1988). "Calibration method for rotating-analyzer ellipsometers." *J. Opt. Soc. Am. A* 5(9): 1466-1471)) can be incorporated into the present disclosed techniques in order to account for the non-ideal behavior of optical components.

While most of the signal equations in the present disclosure have been derived assuming ideal polarizers and other optical elements, it is noted that non-ideal, but well-characterized polarizers (or elements) could also be used. Ultimately, calibration procedures can be used to determine polarizer and sample cell parameters as well as compensator parameters. These procedures could involve separate measurements for each of these components, or a single measurement to account for all of them.

Figure 6:
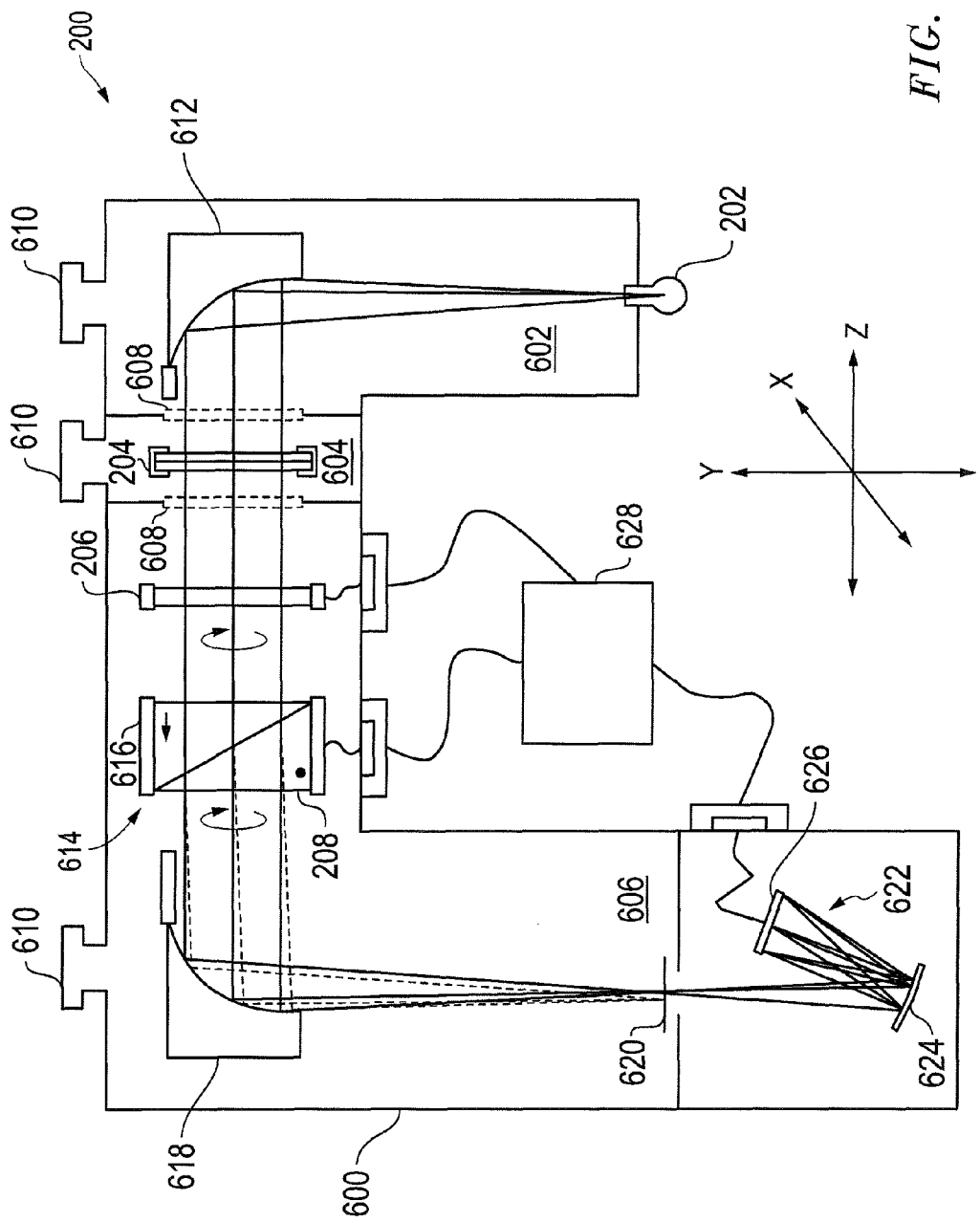
FIG. 6—Detailed representation of an embodiment of FIG. 2.

FIG. 6 presents a detailed schematic of the embodiment 200 shown in FIG. 3. The entirety of the system resides within a leak tight enclosure 600. There are at least three distinct environments which may be configured so that they are isolated or shared; namely, the source module 602, the sample module 604 and the detector module 606. Each module may be equipped with input and output ports, as well as a gas manifold 610 to facilitate the environmental conditioning necessary to sustain VUV operation.

Environmental conditioning is typically achieved through the use of some combination of vacuum, purge, or backfill methodologies to reduce and/or remove the concentration of absorbing species (like oxygen and moisture) so as to support transmission of VUV wavelengths. In situations where purge or backfill techniques are utilized, high-purity non-absorbing (at least over the wavelength region of interest) gases like nitrogen, argon or helium may be employed.

To facilitate efficient operation in the VUV careful attention must be paid during the design and manufacture of said instrument to ensure that all materials and methodologies employed are conducive to VUV operation. Specifically, VUV optical surfaces are highly susceptible to adsorbed species like moisture and other airborne molecular contaminants (AMC). Such species can adversely affect system performance and as such, care must be taken to avoid their accumulation.

In operation, light from a broadband VUV source 202 is collected by a first optic 612 which collimates the light and directs it through a short path length sample cell 204. A particularly well suited source is a modified deuterium lamp equipped with a projecting nose and MgF$_2$ window. The projecting nose of the VUV source typically protrudes into the leak tight enclosure through an opening equipped with an appropriate sealing mechanism. In this manner the associated cabling and power supply for the source remain external to the enclosure.

For broad band applications in the VUV, reflective rather than transmissive optics are generally employed in order to avoid chromatic aberrations and absorption losses. Fortunately, high quality off-axis toroidal reflectors can now be inexpensively manufactured using replication techniques. When coated with appropriate thin films (e.g. MgF$_2$ coated aluminum) these elements represent attractive options for VUV optical system design. While other configurations could certainly be used, a particularly useful embodiment of the current invention incorporates a 90° off-axis parabolic reflector to collect light from the source. The reflector collimates light from the source and directs it towards the sample cell.

The sample cell is housed in a sample module whose environment may be controlled independent of the rest of the system. Preferably, the sample module may be equipped with configurable gate valves 608 on either side of the sample which may be opened or closed. When open, the environment in the sample module is shared with that of the rest of the system and light is allowed to pass through the sample cell. When closed, the environment in the sample module is isolated from the rest of the system and can be independently configured through a gas manifold which provides access to vacuum, backfill and purging capabilities. In this manner, samples may be loaded into or unloaded from the sample module without compromising the environments of the source and detector modules. Hence, when a new sample is loaded the environment within the sample module can be adequately conditioned before the gate valves are opened and the environments are shared.

Alternatively, the sample module may be configured with VUV transparent windows to allow light to pass through the sample cell without sharing the environment of the sample module with the rest of the system. While providing a means for isolating the environment within the sample module, this configuration has the drawback of introducing additional elements in the optical path. These additional elements may complicate system calibration and operation, rendering data analysis more difficult.

Light exiting the short path length sample cell passes through a VUV compensator 206. The compensator is mounted on a rotary stage so that the phase difference imparted upon the ordinary and extraordinary components of the incident beam may be adjusted. The rotary stage connects with an appropriate controller and computer via a vacuum compatible cable assembly. In one preferred embodiment the compensator is continuously rotated during measurement.

Light passing through the compensator encounters a VUV polarizer 614. While several VUV polarizers are commercially available, a particularly well suited version has been recently described in a concurrently filed U.S. Patent Application filed the same date as this application, entitled Polarization Device For Vacuum Ultraviolet or Shorter Wavelengths, U.S. patent application Ser. No. 13/184,601, filed Jul. 18, 2011; the disclosure of which is expressly incorporated herein by reference in its entirety. The polarizer 614 may consist in this embodiment of a prism pair 616, focusing optic 618 and spatial aperture 620. In operation, collimated light entering the polarization analyzer impinges on the front face of the prism pair. The prism pair consists of two MgF$_2$ prisms judiciously cut and arranged such that the ordinary and extraordinary rays are split into orthogonal linear polarization states. The prisms may be optically contacted or separated by a small air gap, depending on the power levels anticipated. The first prism (depicted on the right hand side) is cut with its optical axis aligned perpendicular to its entrance face, while the second prism (shown on the left hand side) is cut with its optical axis aligned parallel to its exit face.

The ordinary beam passes through the pair unaltered, while the extraordinary beam undergoes a slight angular deviation at the interface between the two prisms. The prism pair is mounted on a stage capable of rotating about the optical axis of the prism pair. The rotary stage connects with an appropriate controller and computer via a vacuum compatible cable assembly. The ordinary beam is unaffected by rotation of the prism pair, while the extraordinary beam sweeps out a circular exit pattern when the stage is rotated.

The orthogonally polarized beams exit the prism pair and are collected by the focusing optic which focuses them onto the spatial aperture. The ordinary beam is focused to a well defined spot centered over the opening in the spatial aperture, while the extraordinary beam is less ideally focused elsewhere on the solid portion of the aperture. The extraordinary beam is thus blocked, while the ordinary beam passes through and carries on into the spectroscopic detection system 622.

The focusing optic may again be a 90° off-axis parabolic reflector with an aluminum/$MgF_2$ coating, however it is noted that off-axis reflectors with other angles (for example 60° or 30°) may also prove useful here and in other locations throughout the system. In fact, optics employing these lesser angles may actually provide greater alignment tolerance in some situations.

Light passing through the spatial aperture encounters a wavelength dispersive or diffractive element 624, in this case an aberration-corrected flat-field imaging grating. Light incident on the grating is diffracted and focused such that discrete wavelengths are spatially and simultaneously resolved on the surface of a VUV-sensitive detector 626. As such, the system is truly spectroscopic. Preferably, the detector may be some form of an array detector, capable of simultaneously recording data for multiple wavelengths. In a preferred embodiment, the detector may be configurable such that the gain for each element/pixel can be individually adjusted. The detector is coupled to associated control electronics and a computer 628 through use of vacuum compatible cable assembly. While not explicitly shown, the system is equipped with necessary baffles so as to minimize stray light effects.

Since samples, buffers, and detergents all absorb strongly in the VUV, serious consideration must be given to sample cell design. In particular, where VUV operation is desired it is beneficial to minimize the path length of the sample cells. Recent SR CD investigations have employed $CaF_2$ cells with path lengths as short as 2 μm, created via polishing processes (Wien F., Wallace, B. A. (2005). "Calcium Fluoride Micro Cells for Synchrotron Radiation Circular Dichroism Spectroscopy" *Appl. Spectr.* 59(9): 1109-1113). Where measurements at the shorter end of the VUV are concerned, even shorter path length cells may be required.

The measured CD and LD signals depend on the sample concentration and path length traversed through the sample (i.e. the cell path length). It may be desirable to know the molar circular dichroism, $\Delta\epsilon_\pm$, or molar linear dichroism, $\Delta\epsilon$, as these quantities are more intrinsic to the materials composing the sample. The molar quantities can be determined from the measured CD and LD signals using the expressions $$CD = (\ln 10)\Delta\epsilon_\pm c(l/2) \qquad \text{Eqn. 31}$$

$$LD = (\ln 10)\Delta\epsilon c(l/2) \qquad \text{Eqn. 32}$$

where c is the molar concentration and l is the path-length traversed through the medium.

As a consequence, most useful data analysis will require that the precise path length of the sample cell be known and/or determined. For cells with thickness on the order of >1 μm or so, the interference fringe method (Hennessey J. P. Jr., Johnson, W. C. Jr. (1982). "Experimental errors and their effect on analyzying circular dichroism spectra of proteins" *Analytical Biochemistry* 125: 177-188) can be used. Alternatively, the cell can be filled with a liquid of known absorbance, and the path length back-calculated from the transmission spectrum (Miles A. J., Wien, F., Lees, J. G., Rodger, A., Janes, R. W., Wallace, B. A. (2003). "Calibration and standardization of synchrotron radiation circular dichroism and conventional circular dichroism spectrophotometers." *Spectroscopy* 17: 653-661). For even thinner cells alternate methodologies may be required.

Figure 7:
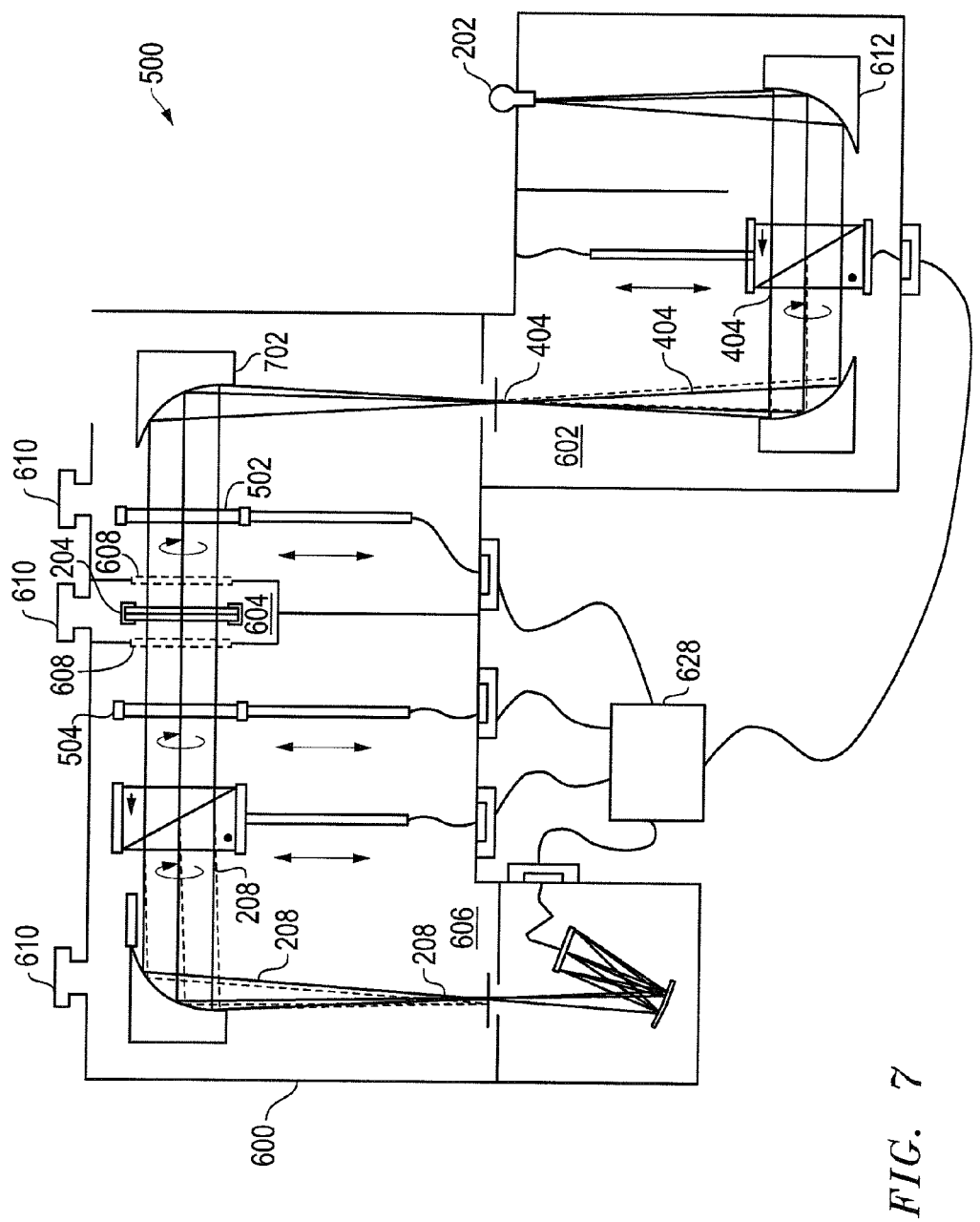
FIG. 7—Detailed representation of an embodiment of FIG. 5.

FIG. 7 shows a more detailed schematic of the highly versatile embodiment 500 of FIG. 5. The system is once again comprised of a source module 602, a sample module 604 and a detector module 606. While the sample and detectors modules appear similar to those of the simpler embodiment of FIG. 6, the source module is somewhat more complicated. In addition to the VUV source 202 and collimating optic 612, the source module of the versatile system in FIG. 7 also includes a VUV polarizer 404 and compensator 502.

In operation light from the source is collected and collimated by a first optic 612. The collimated light travels through the novel polarizer previously described. As in the embodiment of FIG. 6, light traveling through the polarizer is split into ordinary and extraordinary components. The ordinary beam is focused by the second optic and passes through an opening in the spatial aperture. Conversely, the extraordinary beam is focused elsewhere on the aperture and blocked.

Light passing through the aperture is collected by a third optic 702, which collimates it and directs it through a first VUV compensator 502. The compensator and polarizer are mounted in conjunction with both rotary and linear stages. As such, the elements can be rotated during operation or altogether removed from the beam path, essentially reducing the system to the simpler configuration of FIG. 6.

Light passing through the compensator travels through the sample module 604 containing the short path length sample cell 204. The sample module is again equipped with configurable gate valves 608 so as to enable the sample module to be isolated from the rest of the system during sample loading/unloading.

Light exiting the sample chamber passes through the second compensator 504 and polarizer 208. The compensator and polarizer function as previously described and are also equipped with both rotary and linear stages. In this manner the elements may also be removed from the beam path, effectively rendering the system equivalent to that of the simpler embodiment of FIG. 4.

It follows that the versatile embodiment of FIG. 7 may be converted to the embodiments of FIG. 2, 4, or 5, simply by adding or removing polarizers and compensators from the beam path. In this manner, the system may be configured as necessary in order to facilitate the measurement of specific samples. Where complicated samples exhibiting multiple forms of optical anisotropy are concerned, the system of FIG. 7 possesses the necessary flexibility required to facilitate an accurate determination of such. In contrast, when samples exhibiting fewer forms of anisotropy are to be measured, certain elements may be removed thereby simplifying operation (i.e. data acquisition, alignment, calibration, analysis) and improving data quality, particularly at shorter VUV wavelengths.

While not explicitly shown in FIG. 2, 3, 4 or 6, it is noted that these embodiments may also be equipped with means for adding and/or removing optical elements during and/or between measurements.

Generally, all of the embodiments of the present disclosure incorporate a computer that controls the electronic and mechanical components of the system. The instrument control is governed by a main software program, with a user interface allowing a user to issue instructions to the instrument. The instrument mode and measurement "recipe" may be selected by the user but the detailed operation of the instrument (i.e. calibration and data collection) are usually handled automatically by the software program, as is typical for optical instruments. Data analysis for extracting the Fourier coefficients and ultimately the CD from the measured signal (Eqn. 7, etc.) are also typically performed by the software program.

While the ability to provide CD and LD spectra is useful in and of itself, it may be desirable to further analyze the spectra in order to determine more information about the sample. For example, CD spectra of protein solutions are often analyzed in order to determine information about the protein secondary structure. The protein secondary structure is usually estimated by relating the experimental spectrum to a reference set of spectra measured for proteins of known secondary structure. The CD spectrum is assumed to be linearly related to component basis spectra representing pure samples of each structure type:

$$C_\lambda = \Sigma f_k B_{k\lambda} \qquad \text{Eqn. 33}$$

where $C_\lambda$ is the spectrum to be analyzed for the protein sample, $B_{k\lambda}$ is the component basis spectra corresponding to secondary structure k, and $f_k$ is the fractional weight of secondary structure k. The analyzed spectra are usually molar CD, as opposed to the directly measured CD spectra, which also depend on sample concentration and cell path length.

In practice, the component spectra are usually not determined experimentally, but are instead derived from a larger reference set of proteins having known structure. Several methods have been developed to relate the reference spectra to component spectra. Three of the most popular are the SELCON3 method (Sreerema, N., Woody, R. W. (1993). "A self-consistent method for the analysis of protein secondary structure from circular dichroism." *Anal. Biochem.* 209: 32-44; Sreerama, N., Woody, R. W. (2000). "Estimation of protein secondary structure from circular dichroism spectra: comparison of CONTIN, SELCON, and CDSSTR methods with an expanded reference set." *Anal. Biochem.* 287: 252-260), the CDSSTR method (Johnson, W. C. (1999). "Analyzing Protein CD for Accurate secondary Structures." *Proteins: Str. Func. Genet.* 35:307-312), and the CONTIN method (Provencher S. W., Glockner, J. (1981). "Estimation of globular protein secondary structure from circular dichroism." *Biochemistry* 20: 33-37).

These and other methods of data analysis can be integrated into the main computer program, allowing the user to further analyze the CD spectra obtained using the present disclosed techniques. The analysis package can include management of the reference protein spectra databases used in the above mentioned analysis techniques. The database can incorporate reference spectra from the literature or from publicly available databases. The user can also use the present disclosed techniques to construct new databases by measuring samples of known secondary structure. Regardless of whether an existing reference set is incorporated, or a new one created, protein samples of unknown secondary structure can be measured using the present disclosed techniques and analyzed against the reference set.

While embodiments of the present disclosure may be beneficial when employed in stand-alone laboratory use, it is noted that other embodiments may also prove beneficial in applications wherein the present embodiments are integrated into a beam line at a synchrotron radiation facility. In such cases it is likely that one or more optical elements may be added or removed from the system. For example, one or more depolarizers may be added to any of the preferred embodiments or one or more polarizers may be removed.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as presently preferred embodiments. Equivalent elements may be substituted for those illustrated and describe herein and certain features of the invention may be utilized independently of the use of other features, all as would be apparent to one skilled in the art after having the benefit of this description of the invention.

What is claimed is:

1. A spectroscopic circular dichroism instrument, comprising:
a light source which generates a multi-wavelength light beam comprised of light of a plurality of wavelengths;
a region of the spectroscopic circular dichroism instrument for the placement of a sample from which a circular dichroism measurement is to be obtained by exposure of a sample to the multi-wavelength light beam;
a constant phase difference compensator optically coupled to the multi-wavelength light beam, the constant phase difference compensator introducing a phase difference between two orthogonal polarization components of the multi-wavelength light beam;
an optical element coupled to the multi-wavelength light beam, the optical element selecting a linearly polarized component of the multi-wavelength light beam; and
a detector coupled to the multi-wavelength light beam to provide a circular dichroism measurement of the sample, the instrument being capable of providing the circular dichroism measurement simultaneously for multiple wavelengths,
wherein the compensator is rotatable,
wherein circular dichroism spectra and linear dichroism spectra are extracted from a detected intensity signal, and
wherein circular dichroism spectra are extracted from dc and 2ω components of the detected intensity signal and linear dichroism spectra are extracted from the dc and 4ω components of the detected intensity signal, wherein ω is an angular frequency of the compensator rotation.

2. The spectroscopic circular dichroism instrument of claim 1, wherein an optical path of the instrument is configured to allow the multi-wavelength light beam to pass through the constant phase difference compensator and the optical element before exposure of the sample to the multi-wavelength light beam.

3. The spectroscopic circular dichroism instrument of claim 1, where the constant phase difference compensator provides a circular polarization component to the multi-wavelength light beam.

4. The spectroscopic circular dichroism instrument of claim 1, wherein the sample is a protein solution.

5. The spectroscopic circular dichroism instrument of claim 4, wherein the spectroscopic circular dichroism instrument is configured to measure the circular dichroism of spectra of the protein solution, the spectroscopic circular dichroism instrument further configured to analyze the circular dichroism spectra to obtain a protein secondary structure.

6. The spectroscopic circular dichroism instrument of claim 1, further comprising a depolarizer coupled to the multi-wavelength light beam.

7. The spectroscopic circular dichroism instrument of claim 1, further comprising a second compensator and second optical element, the second optical element selecting a linearly polarized component of the multi-wavelength light beam.

8. A spectroscopic circular dichroism instrument, comprising:
- a light source which generates a multi-wavelength light beam comprised of light of a plurality of wavelengths;
- a region of the spectroscopic circular dichroism instrument for the placement of a sample from which a circular dichroism measurement is to be obtained by exposure of a sample to the multi-wavelength light beam;
- a compensator optically coupled to the multi-wavelength light beam, the compensator introducing a phase difference between two orthogonal polarization components of the multi-wavelength light beam;
- an optical element coupled to the multi-wavelength light beam, the optical element selecting a linearly polarized component of the multi-wavelength light beam; and
- a detector coupled to the multi-wavelength light beam to provide a circular dichroism measurement of the sample, the instrument being capable of providing the circular dichroism measurement simultaneously for multiple wavelengths, wherein an optical path of the instrument is configured to allow the multi-wavelength light beam to pass through the compensator and the optical element after exposure of the sample to the multi-wavelength light beam,
wherein the compensator is rotatable,
wherein circular dichroism spectra and linear dichroism spectra are extracted from a detected intensity signal, and
wherein circular dichroism spectra are extracted from dc and 2ω components of the detected intensity signal and linear dichroism spectra are extracted from the dc and 4ω components of the detected intensity signal, wherein ω is an angular frequency of the compensator rotation.

9. A spectroscopic circular dichroism instrument, comprising:
- a light source which generates a multi-wavelength light beam comprised of light of a plurality of wavelengths;
- a region of the spectroscopic circular dichroism instrument for the placement of a sample from which a circular dichroism measurement is to be obtained by exposure of a sample to the multi-wavelength light beam;
- a compensator optically coupled to the multi-wavelength light beam, the compensator introducing a phase difference between two orthogonal polarization components of the multi-wavelength light beam;
- an optical element coupled to the multi-wavelength light beam, the optical element selecting a linearly polarized component of the multi-wavelength light beam; and
- a detector coupled to the multi-wavelength light beam to provide a circular dichroism measurement of the sample, the instrument being capable of providing the circular dichroism measurement simultaneously for multiple wavelengths, wherein the compensator is rotatable and provides a circular polarization component to the multi-wavelength light beam,
wherein circular dichroism spectra and linear dichroism spectra are extracted from a detected intensity signal, and
wherein circular dichroism spectra are extracted from dc and 2ω components of the detected intensity signal and linear dichroism spectra are extracted from the dc and 4ω components of the detected intensity signal, wherein ω is an angular frequency of the compensator rotation.

10. A spectroscopic circular dichroism instrument, comprising:
- a light source which generates a multi-wavelength light beam comprised of light of a plurality of wavelengths;
- a region of the spectroscopic circular dichroism instrument for the placement of a sample from which a circular dichroism measurement is to be obtained by exposure of a sample to the multi-wavelength light beam;
- a compensator optically coupled to the multi-wavelength light beam, the compensator introducing a phase difference between two orthogonal polarization components of the multi-wavelength light beam;
- an optical element coupled to the multi-wavelength light beam, the optical element selecting a linearly polarized component of the multi-wavelength light beam; and
- a detector coupled to the multi-wavelength light beam to provide a circular dichroism measurement of the sample, the instrument being capable of providing the circular dichroism measurement simultaneously for multiple wavelengths, wherein the compensator is rotatable,
wherein circular dichroism spectra and linear dichroism spectra are extracted from a rotation dependent intensity signal, and
wherein circular dichroism spectra are extracted from dc and 2ω components of the rotation dependent intensity signal and linear dichroism spectra are extracted from the dc and 4ω components of the rotation dependent signal, wherein ω is an angular frequency of the compensator rotation.

11. A method for performing a dichroism measurement, the dichroism measurement being a circular dichroism measurement, a linear dichroism measurement or both a circular and linear dichroism measurement, comprising:
- generating a light beam comprised of multiple wavelengths;
- exposing a measurement sample with said light beam and passing the light beam through the sample;
- inducing a phase difference between orthogonal polarization components of an emerging light beam emerging from the sample;
- selecting a polarization component of the emerging light beam;
- detecting an intensity of a polarization component output light beam at multiple wavelengths; and
- extracting a dichroism measurement from the intensity of the polarization component output light beam for each of the multiple wavelengths, wherein the phase difference between the orthogonal polarization components is induced by use of an optical compensator,
wherein the optical compensator is rotated during measurement, generating time- and wavelength-dependent intensity data, and
wherein circular dichroism spectra are extracted from dc and 2ω components of a detected intensity signal and linear dichroism spectra are extracted from the dc and 4ω components of the detected intensity signal, wherein ω is an angular frequency of the compensator rotation.

12. The method of claim 11, wherein the dichroism measurement is a circular dichroism measurement.

13. The method of claim 11, wherein the dichroism measurement is a linear dichroism measurement.

14. The method of claim 11, wherein the dichroism measurement is both a circular dichroism measurement and a linear dichroism measurement.

15. The method of claim 11, wherein the sample is a protein solution.

16. The method of claim 15, further comprising analyzing a circular dichroism spectra to obtain data regarding a protein secondary structure.

17. The method of claim 11, wherein the polarization component is selected by use of an analyzer/polarizer.

* * * * *